United States Patent [19]

Tamaki et al.

[11] 4,126,686
[45] Nov. 21, 1978

[54] ANALGESIC 3-(3-METHYL-3-BUTENYL)-1,2,3,4,5,6-HEX-AHYDRO-6,11-DIMETHYL-8-HYDROXY-2,6-METHANO-3-BENZAZOCINE

[75] Inventors: Kentaro Tamaki; Naoki Naito; Fumio Nishimura; Kyoichi Fujii, all of Sakai; Nobuo Nakamura, Sunto, all of Japan

[73] Assignee: Kyowa Hakko Kogyo Kabushiki Kaisha, Otemachi, Japan

[21] Appl. No.: 753,331

[22] Filed: Dec. 22, 1976

[30] Foreign Application Priority Data

Jan. 1, 1976 [JP] Japan ............................ 51-144
Jul. 12, 1976 [JP] Japan .......................... 51-82750

[51] Int. Cl.$^2$ ................. C07D 221/26; A61K 31/445
[52] U.S. Cl. ................. 424/267; 260/570.6; 546/97; 546/216
[58] Field of Search .............. 260/293.54, DIG. 13; 424/267

[56] References Cited

U.S. PATENT DOCUMENTS 3,250,678  5/1966  Archer ........................ 260/293.54

OTHER PUBLICATIONS

Capon, B. et al., *Organic Reaction Mechanisms,* Interscience Publishers, New York 1971, pp. 262-263.
Chemical Abstracts, 74, 76345q (1971) [German Offen. 1,960,839].
Chemical Abstracts, 82, 170731z (1975) [Japan. Kokai 74,124,068].

Primary Examiner—Henry R. Jiles
Assistant Examiner—Richard A. Schwartz
Attorney, Agent, or Firm—Wolder, Gross & Yavner

[57] ABSTRACT

Disclosed is 3-(3-methyl-3-butenyl)-1, 2, 3, 4, 5, 6-hexahydro-6, 11-dimethyl-8-hydroxy-2, 6-methano-3-benzazocine, a new derivative of benzazocine, which has superior analgesic properties.

14 Claims, 4 Drawing Figures

ANALGESIC 3-(3-METHYL-3-BUTENYL)-1,2,3,4,5,6-HEXAHYDRO-6,11-DIMETHYL-8-HYDROXY-2,6-METHANO-3-BENZAZOCINE

The present invention relates to a new derivative of benzazocine, a process for the production thereof and an analgesic composition containing the new derivative of benzazocine as an active ingredient.

It is well known that certain derivatives of benzazocine exhibit an analgesic activity. In particular, 3-(3-methyl-2-butenyl)-1,2,3,4,5,6-hexahydro-6,11-dimethyl-8-hydroxy-2,6-methano-3-benzazocine (hereinafter designated as pentazocine) represented by the following formula:

has been deeply admired for the sake of its excellent analgesic activity. The present inventors have discovered a new derivative of benzazocine and a process for producing the same and also that the new derivative of benzazocine has unexpectedly a better analgesic activity than the known pentazocine.

An object of the present invention is to provide a new derivative of benzazocine. The present invention provides 3-(3-methyl-3-butenyl)-1,2,3,4,5,6-hexahydro-6,11-dimethyl-8-hydroxy-2,6-methano-3-benzazocine represented by the following formula (I) and acid salts thereof.

The physico-chemical properties of the compound provided by the present invention are as follows.

Melting point: 145°–148° C.

$R_f$ value of thin layer chromatography: 0.65 when developed with isopropyl ether-chloroform-methanol = 9:5:2 (in volume ratio)

Figure 1:
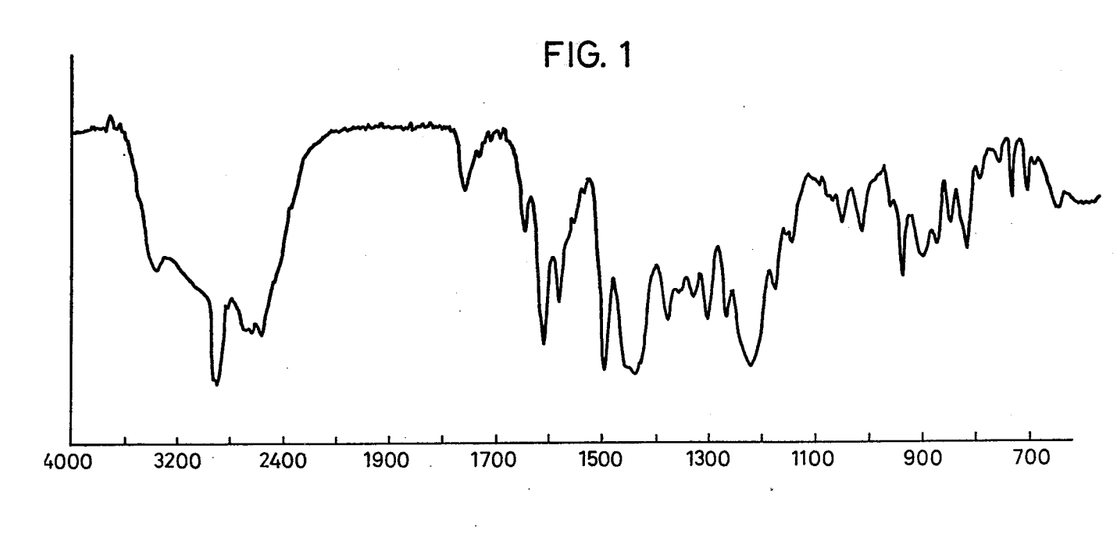
FIGS. 1 and 2 show the IR and NMR spectrum of 3-(3-methyl-3-butenyl)-1,2,3,4,5,6-hexahydro-6,11-dimethyl-8-hydroxy-2,6-methano-3-benzazocine of Example 1.

IR spectrum (KBr): 3400 cm$^{-1}$ (phenolic hydroxyl group), 1750 cm$^{-1}$ (double bonding between terminal C - C atoms) (FIG. 1)

Figure 2:
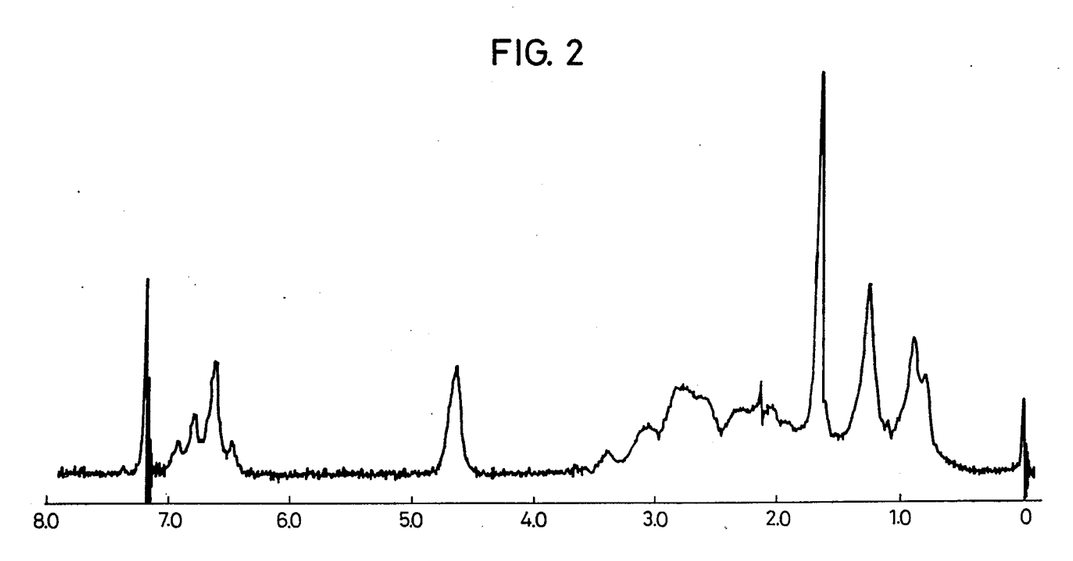

NMR spectrum (in CDCl$_3$) δ(ppm): 0.85 (d, 3H), 1.27 (s, 3H), 1.66 (s, 3H) (FIG. 2)

MS: 230 (base peak)

The above-mentioned properties were compared with the properties of various derivatives of benzazocine of the known types such as pentazocine having the following properties.

Melting point: 150°–151° C.

$R_f$ value of thin layer chromatography: 0.48 when developed with isopropyl ether-chloroform-methanol = 9:5:2 (in volume ratio)

Figure 3:
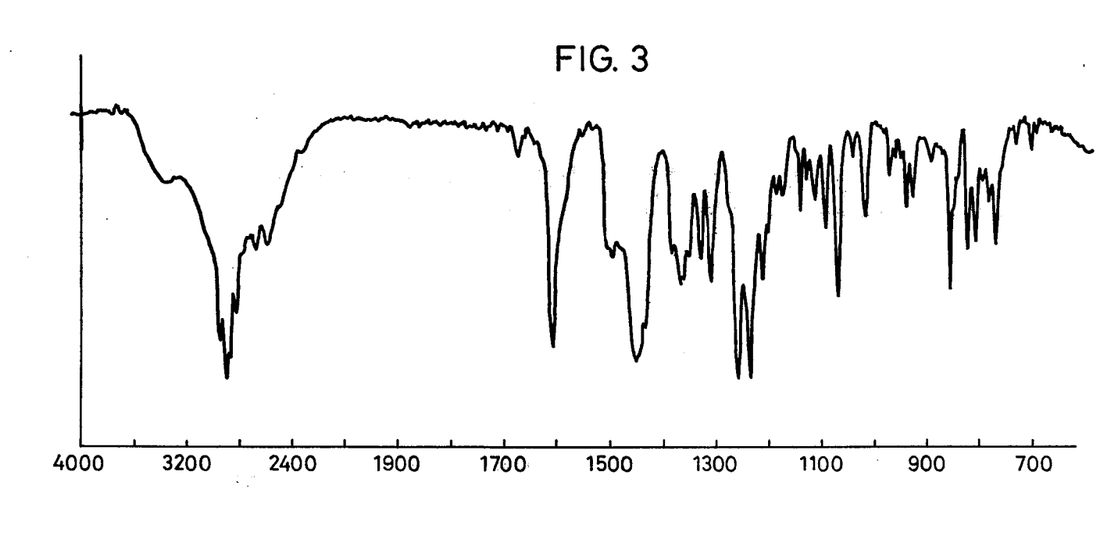
FIGS. 3 and 4 show the IR and NMR spectrum of pentazocine.

IR spectrum (KBr): 3450 cm$^{-1}$, 1670 cm$^{-1}$ (FIG. 3)

Figure 4:
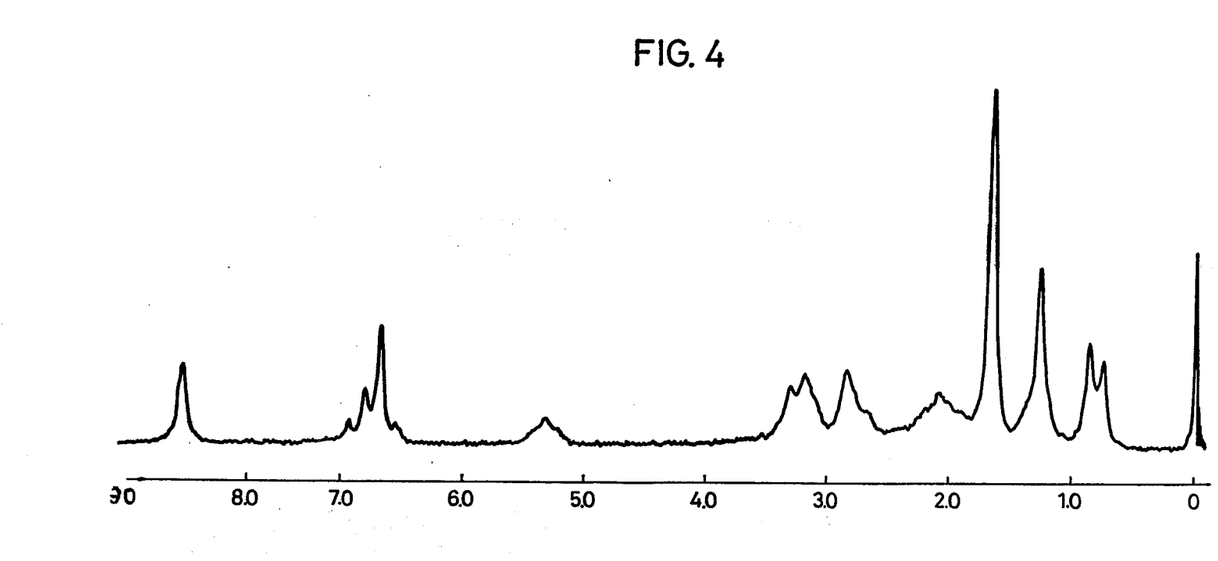

NMR spectrum (in CDCl$_3$) δ(ppm): 0.84 (d, 3H), 1.20 (s, 3H), 1.68 (s, 6H) (FIG. 4)

As a result, it has been confirmed that the derivative provided by the present invention is a new compound which is an isomer of pentazocine and which is represented by the formula (I). The pentazocine used for the above-mentioned comparison and for the undergoing experiments was prepared in the manner which is referred to at the end of this specification.

There are two processes for the preparation of the compound of formula (I). One process is exemplified as follows.

-continued (II)
1-(3-methyl-2-butenyl)-2-(p-hydroxy)-
benzyl-3,4-dimethyl-3-hydroxypiperidine ↓ Reaction III (I)
3-(3-methyl-3-butenyl)-1,2,3,4,5,
6-hexahydro-6, 11-dimethyl-8-hydroxy-2,
6-methano-3-benzazocine.

In the above schematic drawings, $R_1$ is H or an alkyl group (preferably one having 1 to 4 carbon atoms) and $R_2$ is an alkyl group (preferably one having 1 to 4 carbon atoms).

In the above-mentioned steps, Reaction (I) is carried out by subjecting the compound of formula (IV) to the ringclosing reaction in an inert solvent in the presence of a Lewis acid. It is preferable, for conducting the reaction smoothly, to add a base to the reaction system simultaneously with or after addition of the Lewis acid. Preferable Lewis acid catalysts are exemplified by aluminium bromide, boron trichloride, boron tribromide and like. Preferable bases are exemplified by ammonia, pyridine, sodium hydroxide and like. The Lewis acid is used in an amount of from 1 to 10 mols per one mol of the compound of formula (IV) and the base is used in an amount of from 1 to 10 mols per one mol of the Lewis acid. The inert solvents which can be used for Raction (I) are exemplified by chloroform, 1,2-dichloroethane, dichloromethane and like. The reaction is effected at a temperature of from $-70°$ to $100°$ C. for 1 to 10 hours to obtain the compound of formula (III), which can then be purified and isolated in a conventional manner such as e.g. concentration, crystallization, recrystallization, column chromatography and like.

Reaction (II) is carried out by subjecting the compound of formula (III) to the 3-methyl-2-butenylation by using a suitable alkylating method. For example, this reaction is effected by subjecting the compound of formula (II) to the reaction with 3-methyl-2-butenyl bromide in an inert solvent, which can with advantage be carried out in the presence of a basic salt of an alkali metal such as sodium bicarbonate, sodium carbonate and like. 1 To 1.5 mols of 3-methyl-2-butenyl bromide is used per one mol of the compound of formula (III) while 1 to 10 mols of a basic salt of an alkali metal is used per one mol of 3-methyl-2-butenyl bromide. Preferable inert solvents are exemplified by dimethylformamide, dimethylacetamide, dimethylsulfoxide, tetrahydrofuran and like. The reaction is effected at a temperature of from room temperature to the reflux temperature of the used solvent for 1 to 5 hours to obtain the compound of formula (II), which can then be purified and isolated from the reaction mixture in a conventional manner such as e.g. concentration, solvent extraction, crystallization, column chromatography and like.

Reaction (III) is carried out by subjecting the compound of formula (II) to the ring-closing reaction in the presence of a ring-closing agent and with a simultaneous transference of the double bond. As the ring-closing agents, it is preferred to use hydrobromic acid, hydroiodic acid and the like. The ring-closing agent is preferably used in an approximate amount of from 1 to 50 mols per one mol of the compound of formula (II). When hydrobromic acid, hydroiodic acid and the like are used, the ring-closing agent reaction can be carried out without using any solvent because these acids also serve as a solvent. However, it is also possible, for conducting the reaction smoothly, to use any other solvent additionally which are exemplified by water, acetic acid, propionic acid and the like. The reaction is effected at a temperature of from $80°$ to $150°$ C. for 1 to 30 hours. After the completion of the reaction, the compound of formula (I) can be recovered from the reaction mixture in a conventional manner such as e.g. extraction, concentration, crystallization, recrystallization, column chromatography and like.

It is also possible to produce the compound of formula (I) by subjecting pentazocine or an acid addition salt thereof to isomerizing reaction, said acid addition salt being one formed for example with hydrohalogenic acid, oxalic acid, fumaric acid or citric acid. The isomerizing reaction is preferably effected by dissolving pentazocine or its acid salt in alkanoic acid containing hydrogen halogenide at a temperature of from $50°$ to $130°$ C. for 5 minutes to 2 hours. The concentration of hydrogen halogenide in alkanoic acid is preferably 5–27% (w/w) and the amount of hydrogen halogenide-containing alkanoic acid is preferably 4–50 g per 1 g of pentazocine or its acid salt. The compound of formula (I) is isolated from the reaction mixture by neutralizing the excess acid with an aqueous solution of a base such as an aqueous ammonia or an aqueous solution of caustic soda to convert the compound of formula (I) into a free form, extracting it with an organic solvent such as, for example, chloroform and removing off the solvent. The purification is carried out in a conventional manner such as e.g. recrystallization, column chromatography and like.

The compound of formula (I) can be converted into a salt form by subjecting to the reaction with an acid such as e.g. hydrochloric acid, sulfuric acid, hydrobromic acid, oxalic acid, fumaric acid, citric acid and like in a conventional manner.

According to the another aspect of the present invention, there is provided an analgesic composition which contains the compound of formula (I) as active ingredient.

The acute toxicity and pharmacological activity of the compound of formula (I) are apparent from the following experiments.

EXPERIMENT I

Acute toxicity (determined as $LD_{50}$):

The $LD_{50}$ is calculated according to the method of Litchfield and Wilcoxon [J. of Pharmacol. and Exper. Therap., 96, 99 (1949)]. Male mice of the dd strain weighing 19–21 g and male rats of the Wistar strain weighing 80–100 g are used. One group consists of 10 mice or 10 rats. The compound of formula (I) and pentazocine are administered subcutaneously or orally to the test animals which are observed for one week. The results obtained are shown in Table 1.

TABLE 1

| Agent | Test Animal | $LD_{50}$ (mg/kg) Subcutaneous Administration | Oral Administration |
|---|---|---|---|
| Compound of formula (I) | Mouse | 80 (64 – 101) | 205 (166 – 253) |
| Pentazocine | Mouse | 140 (118 – 166) | 305 (259 – 359) |
| Compound of formula (I) | Rat | 61 (39 – 95) | >300 |
| Pentazocine | Rat | 165 (134 – 204) | >400 |

Note:
The numbers in parenthesis show the confidence limits with 5% level of significance.

EXPERIMENT II

Analgesic activity:

(I) Analgesic activity by acetic acid writhing method:

The experiment is carried out according to the method of Koster et al [Fed. Proc., 18, 412 (1959)].

Male mice of the dd strain weighing 19–21 g are used in groups, each consisting of 10 mice. The test compounds, i.e. the compound of formula (I), pentazocine and morphine are administered subcutaneously or orally to the test mice. Immediately after this, 0.2 ml of a 0.7% (v/v) aqueous solution of acetic acid is administered intraperitoneally to the test mice except those which has been administered orally with morphine, to which 0.2 ml of a 0.7% (v/v) aqueous solution of acetic acid is administered intraperitoneally at 15 minutes after a morphine administration. The mice of a control group are not administered with the test compounds but with only the acetic acid solution in a similar manner to that described above. At 10 minutes after the administration of acetic acid, the number of writhes is counted for 10 minutes. When the writhing numbers of the test group decrease to below 50% of the corresponding numbers of the control group, the test compound is determined to be analgesically active. $ED_{50}$ is calculated according to the method of Litchfield and Wilcoxon [J. Pharmacol. & Exper. Therap., 96, 99 (1949)]. The results obtained are shown in Table 2.

TABLE 2

| Agent | $ED_{50}$ (mg/kg) Subcutaneous Administration | Oral Administration |
|---|---|---|
| Compound of formula (I) | 0.09 (0.07 – 0.11) | 14.3 (10.6 – 19.3) |
| Pentazocine | 3.45 (2.52 – 4.73) | 82 (62 – 109) |
| Morphine | 0.56 (0.41 – 0.77) | 5.1 (3.9 – 6.6) |

Note:
The numbers in parenthesis show the confidence limits with 5% level of significance.

(II) Analgesic activity by Tail Flick method:

The experiment is carried out according to the method of Tail Flick (D'Amour-Smith method) [J. Pharmacol., 72, 74 (1941)].

A light beam of an infrared lamp (100 V; 250W) is passed through a hole having a diameter of a half inch and is irradiated onto the end of the tail of each mouse (male dd strain; weight: 19–21 g) to effect a heat stimulation. The mice which exhibit a flick reaction within 4-6 seconds after the irradiation are collected to make groups, each consisting of 10 mice. The compound of formula (I), pentazocine or morphine is administered subcutaneously to the mice. At 15, 30, 60, 90 and 120 minutes after the administration, the heat stimulation is repeatedly carried out to the mice in a similar manner to that described above and after each heat stimulation the time until the flick reaction occurs is measured. When it is at least once observed that the time until the flick reaction occurs is longer by two times than the corresponding time before the administration of the compound, the compound is determined to be analgesically active. $ED_{50}$ is calculated according to the above-mentioned method of Litchfield and Wilcoxon. The results obtained are shown in Table 3.

TABLE 3

| Agent | $ED_{50}$ (mg/kg) |
|---|---|
| Compound of formula (I) | 0.76 (0.64 – 0.90 |
| Pentazocine | >40 |
| Morphine | 5.2 (4.5 – 6.0) |

Note:
The numbers in parenthesis show the confidence limits with 5% level of significance.

(III) Analgesic activity by tail pinch method:

The experiment is carried out according to the method of H. Takagi et al [Jap. J. Pharmacol., 16, 287 (1966)].

In this experiment, male mice of the dd strain weighing 19–21 g are used in groups, each consisting of 10 mice. Before the experiment, animals which are sensitive to pressure stimulation are selected in the following manner.

An artery clip (pressure: 400 g) is applied to the root of the tail of each mouse, and the mice which exhibit an action for biting the clip by head-turning within 6 seconds from the application of the clip are selected. The compound of formula (I), pentazocine or morphine is administered subcutaneously or orally to the selected mice. At 15, 30, 60, 90, and 120 minutes after the administration, an artery clip is repeatedly applied to the root of the tail of each mouse. In the case that the mouse does not show an action for biting the clip within 6 seconds from one or more of 5 applications of the clip, the test compound is determined to be analgesically active. $ED_{50}$ is calculated according to the method of Litchfield and Wilcoxon [J. Pharmacol. & Exper. Therap., 96, 99 (1949)]. The results obtained are shown in Table 4.

TABLE 4

| Agent | $ED_{50}$ (mg/kg) | |
|---|---|---|
| | Subcutaneous Administration | Oral Administration |
| Compound of formula (I) | 0.51 (0.43 – 0.60) | 29.3 (22.9 – 37.5) |
| Pentazocine | >40 | >40 |
| Morphine | 3.5 (2.7 – 4.6) | 35.5 (25.4 – 49.7) |

Note:
The numbers in parenthesis show the confidence limits with 5% livel of significance.

(IV) Analgesic activity by bradykinin method:

The experiment is carried out according to the method of Abe et al [Nihon Yakuri Gakkai Si (J. Japanese Pharmacological Academy) 67, 9 (1971)].

In this experiment, male rats of the Wistar strain weighing 210–260 g were used in groups, each consisting of 10 rats. A cannula is inserted into the right carotid artery of the rat anesthetized with ether. After recovering completely from ether anesthesis, 0.2 ml of a physiological salt solution containing bradykinin in an amount of about 2 μg/ml is injected retrogradely to the rat through the cannula. Immediately after this, the rat exhibits three symptoms i.e. flexion of the right foreleg, right rotation of the head and motor excitation. The compound of formula (I), pentazocine or morphine is administered subcutaneously or orally to the rat. At 15, 30, 60, 90 and 120 minutes after the administration of the test compound, bradykinin is injected repeatedly to the rat in a similar manner to that described above. When the rat does not exhibits consecutively twice or more the above-mentioned two or three symptoms, the test compound is determined to be analgesically active. $ED_{50}$ is calculated according to the method of Litchfield and Wilcoxon [J. Pharmacol. & Exper. Therap., 96, 99 (1949)]. The results obtained are shown in Table 5.

TABLE 5

| Agent | $ED_{50}$ (mg/kg) | |
|---|---|---|
| | Subcutaneous Administration | Oral Administration |
| Compound of formula (I) | 0.38 (0.27 – 0.54) | 35 (25 – 49) |
| Pentazocine | 10.5 ( 7.2 – 15.2) | >100 |
| Morphine | 4.8 (3.9 – 5.9) | 85 (58 – 125) |

Note:
The numbers in parenthesis show the confidence limits with 5% level of significance.

The usefulness of the compound as medicament is expressed by margin of safety (R) of the compound which is calculated by ($LD_{50}/ED_{50}$). Compounds having higher R are deemed to be more useful as medicament than those having lower R. The margins of safety of the compound of formula (I) and pentazocine are shown in Table 6.

TABLE 6

| Method of Measuring Analgesic Activity | | Margin of Safety (R) | | |
|---|---|---|---|---|
| | | The compound of formula (I) ($R_1$) | Pentazocine ($R_2$) | $R_1/R_2$ |
| Acetic acid | S.C. in mouse | 889 | 40.6 | 21.9 |
| Writhing | P.O. in mouse | 14.3 | 3.7 | 3.9 |

TABLE 6-continued

| Method of Measuring Analgesic Activity | | Margin of Safety (R) | | |
|---|---|---|---|---|
| | | The compound of formula (I) ($R_1$) | Pentazocine ($R_2$) | $R_1/R_2$ |
| Bradykinin | S.C. in rat | 161 | 15.7 | 10.2 |

Note:
S.C. Subcutaneous administration
P.O. Oral administration

The compound of formula (I) or an acid salt thereof as active ingredient is administered either orally for example in the form of tablet or powder or non-orally for example in the form of injection agent or through rectum in the form of suppository. For a mammal weighing about 50 kg suitable daily dosages of the compound of formula (I) or an acid salt thereof are 0.2–16 mg per one kg of weight in the case of oral administration and 0.1–2.4 mg in the case of non-oral administration. Preferable dosages of the compound of formula (I) or an acid salt thereof at once are 0.2–2 mg per one kg of weight in oral administration and 0.1–0.3 mg in non-oral administration. In either case, it is possible, if desire, to administer repeatedly at an interval of from 3 to 6 hours.

In the case of tablet, it is preferred that one tablet contains 10–50 mg of the compound of formula (I) or an acid salt thereof as active ingredient together with other ingredients such as, for exampe, excipient (e.g. lactose, sucrose, starch and like), disintegrators (e.g. starch, crystallized cellulose, calcium cellulose glycolate and like), binders (e.g. starch, polyvinyl alcohol, gum arabic and like), lubricants (e.g. magnesium stearate, talc and like), coating agents (e.g. methyl cellulose, ethyl cellulose, shellac and like), plasticizers (e.g. glycerol and like) and where permitted coloring matter [e.g. Food Red No. 106 [chemical name: monosodium salt of 9-(2'-sulfonium-4'-sulfophenyl)-6-diethylamino-3-(N,N-diethylimino)-3-isoxanthene], Food Yellow No. 4 [chemical name: trisodium salt of 3-carboxy-5-hydroxy-1-(p-sulfophenyl)-4-(p-sulfophenylazo)pyrazole] and like].

In the case of powders, 1–10% (w/w) of the compound of formula (I) or an acid addition salt thereof is preferably contained as active ingredient together with other ingredients such as excipient (e.g. lactose, glucose, sucrose and like).

In the case of injection agent, it is preferred that 5–15 mg of the compound of formula (I) or an acid addition salt thereof as active ingredient is dissolved in 1–3 ml of distilled water together with other ingredients such as, for example, lactose which may be used to assist the dissolution of the compound of formula (I).

In the case of suppository, the compound of formula (I) or an acid addition salt thereof as active ingredient is mixed with a water-soluble vehicle such as, for example, carbowax, glycerogelatin and like and a fat-soluble vehicle such as, for example, Witepsol, cacao wax, laurin wax and like so that each piece contains 5–15 mg of the compound of formula (I).

The following non-limitative examples illustrate the invention.

EXAMPLE 1

14 G of 1-(p-methoxy) phenyl-2-amino-3,4-dimethyl-6-ethoxy-3-hexanol represented by formula (IV) is dissolved in 150 ml of dichloromethane. The solution is cooled to −10° C. and kept at this temperature for a short period of time. To this solution is added in one hour 40 g boron tribromide dissolved in 150 ml of dichloromethane. The solution is kept at −10° C for one hour and is then heated slowly to 20° C. The solution is kept at this temperature for 2 hours and then at 40° C. for one hour, followed by ice-cooling to about 0° C. The solution is added with a mixture of ice and aqueous ammonia to giveh an alkaline pH. The combined mixture is allowed to stand for separation of the phases from each other. The dichloroethane lower layer is taken out and concentrated to yield an oily substance, which is then added with ether for the crystallization whereby 7 g of crystals is obtained. The crystals have the following physico-chemical properties.

Melting point: 153°–156° C.

| Elementary analysis: | C(%) | H(%) | N(%) |
|---|---|---|---|
| Found: | 71.31 | 9.05 | 5.98 |
| Calculated as $C_{14}H_{21}NO_2$: | 71.46 | 8.99 | 5.95 |

From the above properties, the crystals are estimated to be 2-(p-hydroxy) benzyl-3,4-dimethyl-3-hydroxypiperidine represented by formula (III).

18.1 G of 2-(p-hydroxy) benzyl-3,4-dimethl-3-hydroxypiperidine represented by formula (III) obtained is dissolved in 200 ml of dimethylformamide. To this solution is added 12.3 g of 3-methyl-2-butenyl bromide and 10 g of sodium bicarbonate and is refluxed for 2 hours. After the reflux, the solvent is evaporated, and 100 ml of water and 100 ml of chloroform are added to the residue. The chloroform layer is separated, washed with water, dehydrated with sodium sulfate and concentrated. The residue is subjected to crystallization from a mixture of methyl ethylketone and ether to obtain 20.3 g of crystals having the following properties.

Melting point: 175°–177° C.

| Elementary analysis: | C(%) | H(%) | N(%) |
|---|---|---|---|
| Found: | 75.56 | 9.81 | 4.59 |
| Calculated as $C_{19}H_{29}NO_2$: | 75.21 | 9.63 | 4.62 |

$R_f$ value of thin layer chromatography [silica gel F 254 (available from Merck & Co., U.S.A.) 5 × 10 cm]: 0.5 when developed with chloroform-methanol-acetic acid = 90:10:5 (in volume ratio) (coloring agent: $I_2$)

From the above properties, the crystals are found to be 1-(3-methyl-2-butenyl)-2-(p-hydroxy) benzyl-3,4-dimethyl-3-hydroxypiperidine represented by formula (II).

To 10 g of the thus-obtained compound of formula (II) is added 150 ml of 49% (w/w) hydrogen iodide aqueous solution and the mixture is subjected to the reaction at a temperature of within the range of 130°–140° C. for 5 hours. The reaction mixture is added with aqueous ammonia to give an alkaline pH and then extracted with chloroform. The chloroform layer is washed with water, dehydrated with sodium sulfate and then concentrated. The residue is recrystallized from acetone to yield 1.9 g of crystals, of which physicochemical properties are as follows.

Melting point: 145°–148° C.

| Elementary analysis: | C(%) | H(%) | N(%) |
|---|---|---|---|
| Found: | 80.06 | 9.72 | 5.08 |
| Calculated as $C_{19}H_{27}NO$: | 79.95 | 9.53 | 4.91 |

$R_f$ value of thin layer chromatography: 0.65 when developed with isopropyl ether-chloroform-methanol = 9:5:2 (in volume ratio)

IR spectrum (KBr): 3400 cm$^{-1}$ (phenolic hydroxyl group), 1750 cm$^{-1}$ (double bonding between terminal C — C atoms) (FIG. 1)

NMR spectrum (in CDCl$_3$) δ(ppm): 0.85 (d, 3H), 1.27 (s, 3H), 1.66 (s, 3H) (FIG. 2)

MS 230 (base peak)

From the above properties, the crystals are identified to be 3-(3-methyl-3-butenyl)-1,2,3,4,5,6-hexahydro-6,11-dimethyl-8-hydroxy-2,6-methano-3-benzazocine represented by formula (I).

1-(p-methoxy)phenyl-2-amino-3,4-dimethyl-6-ethoxy-3-hexanol represented by formula (IV) used as the starting material in this example is a known compound disclosed in JAOS 66624/74.

EXAMPLE 2

500 Mg of pentazocine is dissolved in 6.0 g of 25% (w/w) hydrogen bromide containing acetic acid and heated under reflux for 20 minutes. After cooling, the reaction mixture is poured into an ice-aqueous ammonia and extracted with chloroform. The extract is washed with water and dried with sodium sulfate. After removing the solvent, the residue is subjected to column chromatography [silica gel 20 g; developer: isopropyl ether:chloroform:methanol = 9:5:2 (in volume ratio)]. After discarding the first fraction in an amount of about 30 ml, the following 50 ml of fraction is collected and the solvent is removed. The residue is then dried to obtain 360 mg of powder, of which properties are identical with those of the compound obtained in Example 1. Accordingly, the powder obtained is identified as 3-(3-methyl-3-butenyl)-1,2,3,4,5,6-hexahydro-6,11-dimethyl-8-hydroxy-2,6-methano-3-benzazocine represented by formula (I).

EXAMPLE 3

2.8 G of the compound represented by formula (I) prepared in a similar manner to that described in Example 1 is dissolved in 20 ml of acetone and then added with 1 ml of 35% (w/w) hydrochloric acid. After this, the solvent is removed under reduced pressure to give 3 g of crystals. The crystals are found to be hydrochloride of the compound of formula (I).

EXAMPLE 4

Tablet

500 G of the compound of formula (I), 1.362 g of crystalline cellulose, 19 g of magnesium stearate and 19 g of talc are mixed well in a twin shell blender for 5 minutes. The resulting powder is directly compressed to tablets in a rotary tabletting machine (Model HU-37, commercial product available from Kikusui Seisakusho, Tokyo, Japan) with a 8.0 mm flat-face bevel-edge punch. There are obtained 10,000 tablets, each having a diameter of 8.0 mm, a thickness of 3.0 mm and a weight of 190 mg.

EXAMPLE 5

Powder

100 G of the compound of formula (I) and 900 g of lactose are mixed together in a twin shell blender for 10 minutes to give uniform powders.

EXAMPLE 6

Suppository

15 G of the compound of formula (I) and 1.625 g of Witepsol S-55 (Commercial product available from Dynamit Nobel, Bundesrepublik Deutschland) as a vehicle are combined and heated to 37° C. in a vessel provided with an agitator and a heating device. The mixture is melted and then stirred at a temperature within the range of 35°-37° C. for about 10 minutes. The melted mixture is distributed and packed in 1.9 ml-suppository containers made of a polyvinyl chloride, the inside of which is coated with polyethylene. Each suppository contains 15 mg of the compound of formula (I) and 1,625 mg of Witepsol S-55.

EXAMPLE 7

Injection agent

900 Mg of lactic acid is dissolved in 75 ml of distilled water. To the resultant solution 0.5 g of the compound of formula (I) is added. After adjusting the pH to 4.5 with addition of 1N sodium hydroxide, the solution is made up to 100 ml with distilled water. The solution is filtered by using a membrane filter and the filtrate is distributed into 1 ml-ampules. Air in the ampules is replaced by nitrogen gas and the ampules are sterillized.

EXAMPLE 8

Injection agent

15 G of citric acid is dissolved in 75 ml of distilled water. To the resultant solution 1.5 g of the compound of formula (I) is added. After adjusting the pH to 4.2 with 1N sodium hydroxide, the solution is made up to 100 ml with saline solution. The solution is filtered by using a membrane filter and the filtrate is distributed into 1 ml-ampules. Air in the ampules is replaced by nitrogen gas and the ampules are sterillized.

EXAMPLE 9

Injection agent

6 G of tartaric acid is dissolved in 75 ml of distilled water. To the resultant solution 1.5 g of the compound of formula (I) is added. After adjusting the pH to 4.0 with 1N sodium hydroxide, the solution is made up to 100 ml with distilled water. The solution is filtered by using a membrane filter and the filtrate is distributed into 1 ml-ampules. Air is replaced by nitrogen gas and the ampules are sterillized.

Reference

By using the compound of formula (I), it is possible to prepare pentazocine, for example, by adding 0.1-2 mols of a sulfonic acid to 1 mol of the compound of formula (I) in an inert organic solvent and heating the mixture at a temperature of from 50° to 120° C. for a period of from 1 to 20 hours to effect the isomerization reaction.

Preparation of pentazocine:

5 G of p-toluene sulfonic acid and 200 ml of benzene are added to 10 g of the compound of formula (I). The resultant mixture is refluxed for 18 hours. After this, benzene is removed by evaporation and the residue is adjusted to an alkaline pH with aqueous ammonia. The resultant mixture is extracted with chloroform. The chloroform layer is taken out, washed with water and then dried. After removing chloroform by evaporation, there is obtained 9 g of semicrystalline substance. The substance is subjected to the column chromatography (adsorbent: silica gel G available from Merck & Co., U.S.A.; 70-230 mesh; developer: chloroform:methanol::acetic acid = 90:10:5 in volume ratio). By crystallizing from acetone 4.5 g of crystals is obtained. The physico-chemical properties of the crystals obtained is as follows.

Melting point: 150°-151° C.

| Elementary analysis: | C(%) | H(%) | N(%) |
|---|---|---|---|
| Found: | 79.73 | 9.46 | 5.02 |
| Calculated as $C_{19}H_{27}NO$ : | 79.95 | 9.53 | 4.91 |

$R_f$ value of thin layer chromatography: 0.48 when developed with isopropyl ether-chloroform-methanol = 9:5:2 (in volume ratio)

IR spectrum (KBr): 3450 cm$^{-1}$, 1670 cm$^{-1}$ (FIG. 3)

NMR spectrum (in CDCl$_3$) δ(ppm): 0.84 (d, 3H), 1.20 (s, 3H), 1.68 (s, 6H) (FIG. 4)

The above physico-chemical properties coincide substantially with those of pentazocine preparate. Freezing point depression is not seen when the obtained crystals and pentazocine preparate are subjected together to examination. From the above, the crystals obtained are identified to be 3-(3-methyl-2-butenyl)-1,2,3,4,5,6-hexahydro-6,11-dimethyl-8-hydroxy-2,6-methano-3-benzazocine i.e. pentazocine.

We claim:

1. A compound represented by the formula:

or acid addition salts thereof.

2. An analgesic agent, comprising as an active ingredient an analgesically effective amount of a compound represented by the formula:

or acid addition salt thereof in association with a pharmaceutically acceptable carrier or excipient.

3. A process for preparing a compound represented by the formula:

comprising the steps of subjecting a derivative of 1-phenyl-2-amino-3-hexanol represented by the formula (IV):

(wherein $R_1$ is H or an alkyl group and $R_2$ is an alkyl group) to the ring-closing reaction in an inert solvent in the presence of a Lewis acid to form 2-(p-hydroxy)benzyl-3,4-dimethyl-3-hydroxypiperidine represented by the formula (III):

subjecting the compound of formula (III) to the 3-methyl-2-butenylation to form 1-(3-methyl-2-butenyl)-2-(p-hydroxy)benzyl-3,4-dimethyl-3-hydroxypiperidine represented by the formula (II):

and subjecting the compound of the formula (II) to the ring-closing reaction with a simultaneous transference of the double bond in the presence of a ring-closing agent.

4. An analgesic tablet for oral administration to a mammal comprising an analgesically effective amount of a compound according to claim 1 and a non-toxic excipient.

5. The tablet of claim 4 comprising in addition a binder, a lubricant, a plasticizer and a coating agent, each of the materials being nontoxic to the mammal.

6. The tablet of claim 4 containing from about 10 to about 50 mg of the compound of claim 1, and being suitable for administration to a mammal weighing about 50 kg.

7. An analgesic suppository for administration to a mammal, the suppository comprising as the active analgesic ingredient an analgesically effective amount of a compound in accordance with claim 1 and a nontoxic solid vehicle selected from the group consisting of water-soluble vehicles and fat-soluble vehicles.

8. The suppository of claim 7 containing from about 5 to about 15 mg of said compound, and being suitable for administration to an about 50 kg mammal.

9. Analgesic powder for oral administration to a mammal, the powder comprising from about 1 to about 10 percent by weight of a compound of claim 1, as the active analgesic ingredient and a nontoxic particulate excipient.

10. An injectable analgesic composition solution for subcutaneous administration to a mammal, the composition comprising an analgesically effective amount of an aqueous solution of a compound of claim 1, having a pH of less than about 5, in unit dosage form.

11. The composition of claim 10 comprising a total volume of from about 1 to about 3 ml and containing from about 5 to about 15 mg of the compound of claim 1 for administration to a mammal of about 50 kg in weight.

12. A method of alleviating pain in a mammal comprising administering to a mammal in need of such treatment the composition of claim 2.

13. The method of claim 12 wherein the analgesic composition is administered to the mammal in a total daily amount of from about 0.1 to about 16 mg per kg of body weight.

14. The method of claim 13 wherein the analgesic composition is administered orally or parenterally.

* * * * *